United States Patent
Padia

(10) Patent No.: US 9,975,865 B2
(45) Date of Patent: May 22, 2018

(54) EPOXIDATION PROCESS

(71) Applicant: Scientific Design Company, Inc., Little Ferry, NJ (US)

(72) Inventor: Ashok S. Padia, Glen Rock, NJ (US)

(73) Assignee: Scientific Design Company, Inc., Little Ferry, NJ (US)

( * ) Notice: Subject to any disclaimer, the term of this patent is extended or adjusted under 35 U.S.C. 154(b) by 0 days. days.

(21) Appl. No.: 15/651,191

(22) Filed: Jul. 17, 2017

(65) Prior Publication Data

US 2018/0016248 A1 Jan. 18, 2018

Related U.S. Application Data

(60) Provisional application No. 62/363,671, filed on Jul. 18, 2016.

(51) Int. Cl.
| | |
|---|---|
| *C07D 301/10* | (2006.01) |
| *C07D 303/06* | (2006.01) |
| *B01J 23/04* | (2006.01) |
| *B01J 23/50* | (2006.01) |
| *C01D 17/00* | (2006.01) |

(52) U.S. Cl.
CPC .......... *C07D 301/10* (2013.01); *B01J 23/04* (2013.01); *B01J 23/50* (2013.01); *C01D 17/003* (2013.01); *C07D 303/06* (2013.01)

(58) Field of Classification Search
CPC .. C07D 301/10; C07D 303/06; C01D 17/003; B01J 23/04; B01J 23/50
See application file for complete search history.

(56) References Cited

U.S. PATENT DOCUMENTS

| | | | |
|---|---|---|---|
| 3,563,914 A | | 2/1971 | Wattimena |
| 3,702,259 A | | 11/1972 | Nielsen |
| 4,033,903 A | * | 7/1977 | Maxwell ............. B01J 23/66 502/347 |
| 4,097,414 A | * | 6/1978 | Cavitt ............. B01J 23/66 502/347 |
| 4,125,480 A | * | 11/1978 | Maxwell ............. B01J 23/66 502/25 |
| 4,761,394 A | | 8/1988 | Lauritzen |
| 4,766,105 A | | 8/1988 | Lauritzen |
| 4,908,343 A | | 3/1990 | Bhasin |
| 5,011,807 A | | 4/1991 | Hayden et al. |
| 5,057,481 A | | 10/1991 | Bhasin |
| 5,099,041 A | | 3/1992 | Hayden et al. |
| 5,102,848 A | | 4/1992 | Soo et al. |
| 5,187,140 A | | 2/1993 | Thorsteinson et al. |
| 5,407,888 A | | 4/1995 | Herzog et al. |
| 6,511,938 B1 | * | 1/2003 | Liu ............. B01J 23/8913 502/325 |
| 7,553,980 B2 | | 6/2009 | Rizkalla et al. |
| 2007/0037991 A1 | * | 2/2007 | Rizkalla ............. B01J 21/04 549/533 |
| 2010/0267975 A1 | * | 10/2010 | Habenschuss ....... C07D 301/03 549/536 |
| 2011/0009653 A1 | | 1/2011 | Mazanec et al. |
| 2014/0200357 A1 | * | 7/2014 | Padia ............. C07C 29/106 549/523 |

FOREIGN PATENT DOCUMENTS

| | | |
|---|---|---|
| RU | 2474578 C2 | 11/2011 |
| WO | 0226370 A1 | 4/2002 |
| WO | 2014018474 A1 | 1/2014 |

OTHER PUBLICATIONS

International Search Report dated Nov. 2, 2017 received in a corresponding foreign application.

* cited by examiner

*Primary Examiner* — Timothy R Rozof

(74) *Attorney, Agent, or Firm* — Scully Scott Murphy and Presser

(57) ABSTRACT

A method for producing ethylene oxide comprising: a) providing one or more feed components, wherein the one or more feed components contains at least ethylene obtained by dehydrating ethanol; b) contacting the one or more feed components with an ethylene oxide catalyst bed disposed in a reactor tube, the ethylene oxide catalyst bed comprising: (1) an upstream ethylene oxide catalyst having a first cesium concentration and (2) a downstream ethylene oxide catalyst having a second cesium concentration, wherein the first cesium concentration is higher than the second cesium concentration.

11 Claims, No Drawings

EPOXIDATION PROCESS

CROSS REFERENCE TO RELATED APPLICATION

The present invention claims the benefit of U.S. Provisional Patent Application No. 62/363,671 filed Jul. 18, 2016, the entire content and disclosure of which is incorporated herein by reference.

FIELD OF THE INVENTION

The present invention relates to ethylene oxide production and more particularly to a method of producing ethylene oxide in which a feed including at least ethylene is first provided and thereafter the feed components are contacted with an ethylene oxide catalyst bed disposed in a reactor tube, the ethylene oxide catalyst bed comprising: (1) an upstream ethylene oxide catalyst having a first cesium concentration and (2) a downstream ethylene oxide catalyst having a second cesium concentration, wherein the first cesium concentration is higher than the second cesium concentration.

BACKGROUND OF THE INVENTION

Though present in natural settings at minute quantities, ethylene oxide was first synthesized in a laboratory setting in 1859 by Alsatian chemist Charles-Adolphe Wurtz using the so-called "chlorohydrin" process. However, the usefulness of ethylene oxide as an industrial chemical was not fully understood in Wurtz's time. Industrial production of ethylene oxide using the chlorohydrin process did not begin until the eve of the First World War with the rapid increase in demand for ethylene glycol (of which ethylene oxide is an intermediate) as an antifreeze for use in the rapidly-growing automotive market. Even then, the chlorohydrin process produced ethylene oxide in relatively small quantities and was highly uneconomical.

The chlorohydrin process was eventually supplanted by another process, the direct catalytic oxidation of ethylene with oxygen, the result of a second breakthrough in ethylene oxide synthesis, discovered in 1931 by French chemist Theodore Lefort. Lefort used a solid silver catalyst with a gas phase feed that included ethylene and utilized air as a source of oxygen.

In the eighty years since the development of the direct oxidation method, the production of ethylene oxide has increased so significantly that today it is one of the largest volume products of the chemicals industry, accounting, by some estimates, for as much as half of the total value of organic chemicals produced by heterogeneous oxidation.

Given the foregoing there is a continuing need in the art to optimize the formulation and usage of ethylene oxide catalysts, especially across the range of temperatures, reaction conditions, and reactor feed compositions that they are subjected to in current commercial ethylene oxide reactor units.

BRIEF SUMMARY OF THE INVENTION

A method for producing ethylene oxide comprising: a) providing one or more feed components, wherein the one or more feed components contain at least ethylene; b) contacting the one or more feed components with an ethylene oxide catalyst bed disposed in a reactor tube, the ethylene oxide catalyst bed comprising: (1) an upstream ethylene oxide catalyst having a first cesium concentration and (2) a downstream ethylene oxide catalyst having a second cesium concentration, wherein the first cesium concentration is higher than the second cesium concentration.

A system for producing ethylene oxide comprising: (a) a source of ethylene; (b) an ethylene oxide reactor containing a plurality of reactor tubes; and (c) an ethylene oxide catalyst bed disposed in each reactor tube, the ethylene oxide catalyst bed containing an upstream ethylene oxide catalyst having a first cesium concentration and a downstream ethylene oxide catalyst having a second cesium concentration, wherein the first cesium concentration is higher than the second cesium concentration.

DETAILED DESCRIPTION OF THE INVENTION

All parts, percentages and ratios used herein are expressed by volume unless otherwise specified. All documents cited herein are incorporated by reference.

It has been found in the present invention that the formulation and usage of ethylene oxide catalysts can be optimized by simultaneously using ethylene oxide catalysts having different compositions—in particular two different ethylene oxide catalysts each having a different cesium concentration. This technique and their formulation shall be described in greater detail, below.

Ethylene Oxide Catalysts

The silver-based epoxidation catalysts that can be employed in the present invention includes a support, and at least a catalytically effective amount of silver or a silver-containing compound; also present is a promoting amount of cesium; also optionally present is a promoting amount of rhenium or a rhenium-containing compound; also optionally present is a promoting amount of one or more alkali metals or alkali-metal-containing compounds.

As used herein the term "promoting amount" of a certain component of the catalyst refers to an amount of that component that works effectively to improve the catalytic properties of the catalyst when compared to a catalyst that does not contain that component. Examples of catalytic properties include, inter alia, operability (resistance to runaway), selectivity, activity, conversion, stability and yield. It is understood by one skilled in the art that one or more of the individual catalytic properties may be enhanced by the "promoting amount" while other catalytic properties may or may not be enhanced or may even be diminished.

The support employed in this invention may be selected from a large number of solid, refractory supports that may be porous and may provide the preferred pore structure. Alumina is well known to be useful as a catalyst support for the epoxidation of an olefin and is the preferred support. The support may comprise materials such as alpha-alumina, charcoal, pumice, magnesia, zirconia, titania, kieselguhr, fuller's earth, silicon carbide, silica, silicon carbide, clays, artificial zeolites, natural zeolites, silicon dioxide and/or titanium dioxide, ceramics and combination thereof. The support may comprise at least about 85 wt. % alpha-alumina. The remaining components may include inorganic oxides other than alpha-alumina, such as silica, alkali metal oxides (e.g., sodium oxide) and trace amounts of other metal-containing or non-metal-containing additives or impurities.

Regardless of the choice of the support used, it is usually shaped into particles, chunks, pieces, pellets, rings, spheres, wagon wheels, cross-partitioned hollow cylinders, and the like, of a size suitable for employment in a fixed-bed epoxidation reactor. The support particles can preferably have equivalent diameters in the range from about 3 mm to about 12 mm, and more preferably in the range from about 5 mm to about 10 mm. (Equivalent diameter is the diameter of a sphere having the same external surface (i.e., neglecting surface within the pores of the particle) to volume ratio as the support particles being employed.)

Suitable supports are available commercially. Without being limited to the specific compositions and formulations contained therein, further information on support compositions and methods for making supports may be found, for example, in U.S. Patent Publication No. 2007/0037991.

In order to produce a catalyst for the oxidation of an olefin to an olefin oxide, a support having the above characteristics is then provided with a catalytically effective amount of silver on its surface. In one embodiment, the catalytically effective amount of silver is from 10 weight percent to 50 weight percent. The catalyst is prepared by impregnating the support with a silver compound, complex or salt dissolved in a suitable solvent sufficient to cause deposition of a silver-precursor compound onto the support. Preferably, an aqueous silver solution is used.

In addition to silver, cesium is also deposited or present on the support in a promoting amount. Historically, cesium has offered challenges to those wishing to formulate an ethylene oxide catalyst. This is because the addition of cesium to a catalyst as a promoter increases the selectivity of a catalyst, but at the concomitant cost of decreasing the activity. Thus, when selecting the cesium concentration of an ethylene oxide catalyst, it has historically been necessary for the formulator to reach some compromise between selectivity and activity. This prevents the most efficient possible catalyst from being prepared.

However, in the present invention the preparation of such "compromised" catalysts have been avoided. This has been done by disposing at least two different catalysts of at least two different cesium compositions in the same reactor tubes (the configuration of the reactor and reactor tubes is discussed in greater detail, below). Specifically, in the present invention the reactor tubes contain a packed ethylene oxide catalyst bed divided into two parts: an upstream ethylene oxide catalyst and a downstream ethylene oxide catalyst. The packed ethylene oxide catalyst bed contains from about 10 wt % to about 90 wt % of the upstream ethylene oxide catalyst and about 10 wt % to about 90 wt % of the downstream epoxidation catalyst.

By the "upstream" ethylene oxide catalyst it is meant that the catalyst is placed closer to the reactor inlet and closer to the upper end of the reaction tube. By the "downstream " ethylene oxide catalyst it is meant that the catalyst is farther away from the reactor inlet and closer to the lower end of the reaction tube. (The configuration of the reactor and reactor tubes is discussed in greater detail, below). The upstream ethylene oxide catalyst may be formed directly on top of the downstream ethylene oxide catalyst or alternatively, catalyst inerts or some other spacing mechanism may be interposed between them.

The reactor feed that contacts the "upstream" catalyst (i.e., closer to the reactor inlet) is richer in the primary reaction gases: ethylene oxide and oxygen, because this feed has just begun contacting the catalyst in the catalyst bed and there hasn't been sufficient time for a greater amount of the ethylene and oxygen to react. As one moves "downsteam" through the tube (i.e., closer and closer to the reactor outlet) more and more of the ethylene and oxygen is reacted to form ethylene oxide (as well as carbon dioxide and other by-products). Thus, the concentration of ethylene and oxygen is higher in the upstream portion of the tubes compared with the downstream portions.

In this configuration the upstream ethylene oxide catalyst (which contains a first cesium concentration) and the downstream ethylene oxide catalyst (which contains a second cesium concentration, this second cesium concentration being lower than the first cesium concentration) are each optimized for their specific location inside the reactor tube. Because the upstream ethylene oxide catalyst has a higher cesium content it has a higher selectivity and thus makes better use of the upstream reactor feed which has a higher concentration of oxygen and ethylene; meanwhile as the unreacted portion of the reactor feed passes downstream through the reactor tube it contacts the downstream ethylene oxide catalyst, which has less cesium and is thus more active—the higher activity of the catalyst makes better use of the lower concentrations of the reactants oxygen and ethylene. The above-mentioned first cesium concentration is from about 200 ppm to about 1000 ppm and the above-mentioned second cesium concentration is from about 100 ppm to about 700 ppm; more preferably the first cesium concentration is from about 400 ppm to about 800 ppm and the second cesium concentration is from about 300 ppm to about 600 ppm.

A promoting amount of a rhenium component, which may be a rhenium-containing compound or a rhenium-containing complex may also be deposited on the support, either prior to, coincidentally with, or subsequent to the deposition of the silver. The rhenium promoter may be present in an amount from about 0.001 wt. % to about 1 wt. %, preferably from about 0.005 wt. % to about 0.5 wt. %, and more preferably from about 0.01 wt. % to about 0.1 wt. % based on the weight of the total catalyst including the support, expressed as the rhenium metal.

Other components which may also be deposited on the support either prior to, coincidentally with, or subsequent to the deposition of the silver and rhenium are promoting amounts of an alkali metal or mixtures of two or more alkali metals, as well as optional promoting amounts of a Group IIA alkaline earth metal component or mixtures of two or more Group IIA alkaline earth metal components, and/or a transition metal component or mixtures of two or more transition metal components, all of which may be in the form of metal ions, metal compounds, metal complexes and/or metal salts dissolved in an appropriate solvent. The support may be impregnated at the same time or in separate steps with the various catalyst promoters. The particular combination of support, silver, alkali metal promoter(s), rhenium component, and optional additional promoter(s) of the instant invention will provide an improvement in one or more catalytic properties over the same combination of silver and support and none, or only one of the promoters.

In addition to cesium as mentioned above, other suitable alkali metal promoters may be selected from lithium, sodium, potassium, rubidium, or combinations thereof, with combinations of cesium with other alkali metals being especially preferred. The amount of alkali metal (including cesium) deposited or present on the support is to be a promoting amount. Preferably, the amount ranges from about 10 ppm to about 3000 ppm, more preferably from about 15 ppm to about 2000 ppm, and even more preferably from about 20 ppm to about 1500 ppm, and as especially preferred from about 50 ppm to about 1000 ppm by weight of the total catalyst, measured as the metal.

Suitable alkaline earth metal promoters comprise elements from Group IIA of the Periodic Table of the Elements, which may be beryllium, magnesium, calcium, strontium, and barium or combinations thereof. Suitable transition metal promoters may comprise elements from Groups IVA, VA, VIA, VIIA and VIIIA of the Periodic Table of the Elements, and combinations thereof. Most preferably the transition metal comprises an element selected from Groups IVA, VA or VIA of the Periodic Table of the Elements. Preferred transition metals that can be present include molybdenum, tungsten, chromium, titanium, hafnium, zirconium, vanadium, tantalum, niobium, or combinations thereof.

The amount of alkaline earth metal promoter(s) and/or transition metal promoter(s) deposited on the support is a promoting amount. The transition metal promoter may typically be present in an amount from about 0.1 micromoles per gram to about 10 micromoles per gram, preferably from about 0.2 micromoles per gram to about 5 micromoles per gram, and more preferably from about 0.5 micromoles per gram to about 4 micromoles per gram of total catalyst, expressed as the metal. The catalyst may further comprise a promoting amount of one or more sulfur compounds, one or more phosphorus compounds, one or more boron compounds, one or more halogen-containing compounds, or combinations thereof. The exact concentrations of all promoters mentioned above will, of course, will depend on, among other factors, the desired silver content, the nature of the support, the viscosity of the liquid, and solubility of the particular compound used to deliver the promoter into the impregnating solution.

The silver solution used to impregnate the support may also comprise an optional solvent or a complexing/solubilizing agent such as are known in the art. A wide variety of solvents or complexing/solubilizing agents may be employed to solubilize silver to the desired concentration in the impregnating medium. Useful complexing/solubilizing agents include amines, ammonia, oxalic acid, lactic acid and combinations thereof. Amines include an alkylene diamine having from 1 to 5 carbon atoms. In one preferred embodiment, the solution comprises an aqueous solution of silver oxalate and ethylene diamine. The complexing/solubilizing agent may be present in the impregnating solution in an amount from about 0.1 to about 5.0 moles per mole of silver, preferably from about 0.2 to about 4.0 moles, and more preferably from about 0.3 to about 3.0 moles for each mole of silver.

When a solvent is used, it may be an organic solvent or water, and may be polar or substantially or totally non-polar. In general, the solvent should have sufficient solvating power to solubilize the solution components. At the same time, it is preferred that the solvent be chosen to avoid having an undue influence on or interaction with the solvated promoters. Organic-based solvents which have 1 to about 8 carbon atoms per molecule are preferred. Mixtures of several organic solvents or mixtures of organic solvent(s) with water may be used, provided that such mixed solvents function as desired herein.

The concentration of silver in the impregnating solution is typically in the range from about 0.1% by weight up to the maximum solubility afforded by the particular solvent/solubilizing agent combination employed. It is generally very suitable to employ solutions containing from 0.5% to about 45% by weight of silver, with concentrations from 5 to 35% by weight of silver being preferred.

Impregnation of the selected support is achieved using any of the conventional methods; for example, excess solution impregnation, incipient wetness impregnation, spray coating, etc. Typically, the support material is placed in contact with the silver-containing solution until a sufficient amount of the solution is absorbed by the support. Preferably the quantity of the silver-containing solution used to impregnate the porous support is no more than is necessary to fill the pores of the support. A single impregnation or a series of impregnations, with or without intermediate drying, may be used, depending, in part, on the concentration of the silver component in the solution. Impregnation procedures are described, for example, in U.S. Pat. Nos. 4,761,394, 4,766,105, 4,908,343, 5,057,481, 5,187,140, 5,102,848, 5,011,807, 5,099,041 and 5,407,888. Known prior procedures of pre-deposition, co-deposition and post-deposition of various the promoters can be employed.

After impregnation of the support with the silver-containing compound, i.e., a silver precursor, a rhenium component, an alkali metal component, and the optional other promoters, the impregnated support is calcined for a time sufficient to convert the silver containing compound to an active silver species and to remove the volatile components from the impregnated support to result in a catalyst precursor. The calcination may be accomplished by heating the impregnated support, preferably at a gradual rate, to a temperature in the range from about 200° C. to about 600° C. at a pressure in the range from about 0.5 bar to about 35 bar. In general, the higher the temperature, the shorter the required heating period. A wide range of heating periods have been suggested in the art; e.g., U.S. Pat. No. 3,563,914 discloses heating for less than 300 seconds, and U.S. Pat. No. 3,702,259 discloses heating from 2 hours to 8 hours at a temperature of from 100° C. to 375° C., usually for duration of from about 0.5 hours to about 8 hours. However, it is only important that the heating time be correlated with the temperature such that substantially all of the contained silver is converted to the active silver species. Continuous or step-wise heating may be used for this purpose.

During calcination, the impregnated support may be exposed to a gas atmosphere comprising oxygen, which may be pure oxygen or it may comprise additional components which are inert or non-inert, for example, an inert gas or a mixture of an inert gas with from about 10 ppm to 21% by volume of an oxygen-containing oxidizing component. For purposes of this invention, an inert gas is defined as a gas that does not substantially react with the catalyst or catalyst precursor under the conditions chosen for the calcinations, nitrogen is especially preferred. Further information on catalyst manufacture may be found in the aforementioned U.S. Patent Publication No. 2007/0037991.

Epoxidation Process and Reactor system

The epoxidation process is carried out in a reactor system according to the present invention by continuously contacting an oxygen-containing gas with an olefin, preferably ethylene. Oxygen may be supplied to the reaction in substantially pure molecular form or in a mixture such as air. By way of example, the one or more feed components in the feed mixtures may contain from about 0.5% to about 45% ethylene and from about 3% to about 15% oxygen, with the balance comprising comparatively inert materials including such substances as carbon dioxide, water, inert gases, other hydrocarbons, and the reaction moderators described herein. Non-limiting examples of inert gases include nitrogen, argon, helium and mixtures thereof. Non-limiting examples of the other hydrocarbons include methane, ethane, propane and mixtures thereof. The one or more components of the reaction feed mixture enter the reactor via one or more inlets which are in fluid communication with the source of the components and said inlets are also in fluid communication with the upper ends of the reaction tubes (discussed in greater detail, below). Carbon dioxide and water are byproducts of the epoxidation process as well as common contaminants in the feed gases. Both have adverse effects on the catalyst, so the concentrations of these contaminants are usually kept at a minimum.

Preferably, the pressure in the system is in the range of from about 0 atm to about 50 atm, preferably from about 1 atm to about 35 atm, more preferably from about 1 atm to about 25 atm.

Other of the one or more components of the reaction feed mixture includes one or more chlorine moderators non-limiting examples of which include organic halides such as $C_1$ to $C_8$ halohydrocarbons; especially preferred methyl chloride, ethyl chloride, ethylene dichloride, vinyl chloride or mixtures thereof. Also suitable are hydrogen-free chlorine sources such as perhalogenated hydrocarbons and diatomic chlorine are particularly effective as moderators in gas phase epoxidation. Perhalogenated hydrocarbons refer to organic molecules in which all of the hydrogen atoms in a hydrocarbon have been substituted with halogen atoms; suitable examples are trichlorofluormethane and perchloroethylene. It is important that the concentration level of the moderator be controlled so as to balance a number of competing performance characteristics; for example, moderator concentration levels that result in improved activity may simultaneously lower selectivity. Controlling moderator concentration level is particularly important with the rhenium-containing catalysts of the present invention, because as the rhenium-containing catalysts age the moderator concentration must be carefully monitored so as to continually increase, within very small increments, because optimal selectivity values are obtained only within a narrow moderator concentration range.

A usual method for the ethylene epoxidation process comprises the vapor-phase oxidation of ethylene with molecular oxygen, in the presence of the catalyst, in a fixed-bed tubular reactor. Conventional, commercial fixed-bed ethylene-oxide reactors are typically in the form of a shell and tube heat exchanger containing plurality of parallel elongated reactor tubes in a suitable shell, each tube being approximately 0.7 to 2.7 inches O.D. and 0.5 to 2.5 inches I.D. and 15-53 feet long filled with a packed ethylene oxide catalyst bed and other optional components such as inerts. The reactor will likely contain a plurality of reactor tubes, likely several thousand tubes and as many as twenty thousand. Upper and lower tube sheets are provided to support the multiplicity of tubes, the upper tube sheet being located at the upper end each reactor tube, and the lower tube sheet being located at the lower end of each reactor tube. In practice, the reactor feed in the form of reaction gas components, e.g., ethylene, oxygen, ballast gas (and other aforementioned feed components) are introduced into the reactor through one or more reactor inlets, enter through an upper inlet head located adjacent to the upper end of the reactor tubes and pass at reaction conditions through reactor tubes which are packed with an appropriate silver catalyst. Heat of reaction is removed by a circulating heat transfer fluid such as water which is introduced to the shell side of reactor. Olefin oxide, un-used reactants, and byproducts exit the reactor through a reactor outlet.

Typical operating conditions for the ethylene epoxidation process involve temperatures in the range from about 180° C. to about 330° C., and preferably, from about 200° C. to about 325° C., and more preferably from about 225° C. to about 280° C. The operating pressure may vary from about atmospheric pressure to about 30 atmospheres, depending on the mass velocity and productivity desired. Higher pressures may be employed within the scope of the invention. Residence times in commercial-scale reactors are generally on the order of about 2 seconds to about 20 seconds.

The resulting ethylene oxide, which exits the reactor through the reactor outlet, is separated and recovered from the reaction products using conventional methods. For this invention, the ethylene epoxidation process may include a gas recycle wherein substantially all of the reactor effluent is readmitted to a reactor inlet after substantially or partially removing the ethylene oxide product and the byproducts including carbon dioxide.

The previously-described catalysts have been shown to be particularly selective for oxidation of ethylene with molecular oxygen to ethylene oxide especially at high ethylene and oxygen conversion rates. The conditions for carrying out such an oxidation reaction in the presence of the catalysts of the present invention broadly comprise those described in the prior art. This applies to suitable temperatures, pressures, residence times, diluent materials, moderating agents, and recycle operations, or applying successive conversions in different reactors to increase the yields of ethylene oxide. The use of the present catalysts in ethylene oxidation reactions is in no way limited to the use of specific conditions among those which are known to be effective.

For purposes of illustration only, the following are conditions that are often used in current commercial ethylene oxide reactor units: a gas hourly space velocity (GHSV) of 1500-10,000 $h^{-1}$, a reactor inlet pressure of 10-25 atm, a coolant temperature of 180-315° C., an oxygen conversion level of 10-60%, and an EO production rate (work rate) of 7-20 lbs. EO/cu.ft. catalyst/hr. The feed composition in the reactor inlet after the completion of start-up and during normal operation typically comprises (by volume %) 1-40% ethylene, 3-12% $O_2$; 0.3% to 20%, preferably 0.3 to 5%, more preferably 0.3 to 1% of $CO_2$; 0-3% ethane, an amount of one or more chloride moderators, which are described herein; and the balance of the feed being comprised of argon, methane, nitrogen or mixtures thereof. The ethylene may be derived from any suitable source. One suitable source for obtaining ethylene is from petroleum sources, especially preferred petroleum sources are naptha and ethane from which ethylene can be obtained by, e.g., thermal cracking with steam.

Another suitable source for the ethylene is ethanol, especially preferred is ethanol produced from biomass material ("bioethanol"). Bioethanol itself is obtained by fermentation of vegetable biomass and agricultural byproducts and wastes—and thus is abundant and renewable. The fermentation of biomass to ethanol results in mixtures containing about 95% water and 5% ethanol. The water is then separated out using a combination of azeotropic distillation or solvent extraction. Whatever the source of the ethanol, having provisioned the ethanol, the ethanol is then vaporized by steam and further pre-heated to a suitable reaction temperature in a furnace. The pre-heated vaporized ethanol is then passed to a reactor where the ethanol is dehydrated to ethylene as it passes over the dehydration catalyst.

It will be appreciated by those skilled in the art that changes could be made to the embodiments described above without departing from the broad inventive concept thereof. It is understood therefore that this invention is not limited to the particular embodiments disclosed, but it is intended to cover modifications within the spirit and scope of the present invention as defined by the appended claims.

What I claim is:

1. A method for producing ethylene oxide comprising:
a) providing one or more feed components, wherein the one or more feed components contain at least ethylene;
b) contacting the one or more feed components with an ethylene oxide catalyst bed disposed in a reactor tube, the ethylene oxide catalyst bed comprising: (1) an upstream ethylene oxide catalyst having a first cesium concentration and (2) a downstream ethylene oxide catalyst having a second cesium concentration, wherein the first cesium concentration is higher than the second cesium concentration.

2. The method of claim 1, wherein the ethylene is obtained by dehydrating ethanol.

3. The method of claim 1, wherein the ethylene is obtained from petroleum sources.

4. The method of claim 1, wherein the ethylene oxide catalyst bed comprises from about 10 wt % to about 90 wt % of the upstream ethylene oxide catalyst and about 10 wt % to about 90 wt % of the downstream epoxidation catalyst.

5. The method of claim 1, wherein the first cesium concentration is from about 200 ppm to about 1000 ppm and the second cesium concentration is from about 100 ppm to about 700 ppm.

6. The method according to claim 1, wherein the one or more feed components further comprises oxygen and a ballast gas.

7. A system for producing ethylene oxide comprising:
(a) a source of ethylene;
(b) an ethylene oxide reactor containing a plurality of reactor tubes; and
(c) an ethylene oxide catalyst bed disposed in each reactor tube, the ethylene oxide catalyst bed containing an upstream ethylene oxide catalyst having a first cesium concentration and a downstream ethylene oxide catalyst having a second cesium concentration, wherein the first cesium concentration is higher than the second cesium concentration.

8. The system of claim 7, wherein the upstream silver-containing epoxidation catalyst comprises from about 10 wt % to about 90 wt % of the epoxidation catalyst bed and the downstream silver-containing epoxidation catalyst comprises from about 10 wt % to about 90 wt % of the epoxidation catalyst bed.

9. The system of claim 7, wherein the first cesium concentration is from about 200 ppm to about 1000 ppm and the second cesium concentration is from about 100 ppm to about 700 ppm.

10. The system of claim 7, wherein the ethylene is obtained by dehydrating ethanol.

11. The system of claim 7, wherein the ethylene is obtained from petroleum sources.

* * * * *